(12) United States Patent
Morrison et al.

(10) Patent No.: US 6,280,445 B1
(45) Date of Patent: Aug. 28, 2001

(54) MULTI-AXIAL BONE ANCHOR SYSTEM

(75) Inventors: Matthew M. Morrison, Cordova; B. Thomas Barker; John Stewart Young, both of Memphis; Jeffrey W. Beale, Arlington; Chris E. Johnson, Germantown, all of TN (US)

(73) Assignee: SDGI Holdings, Inc., Wilmington, DE (US)

( * ) Notice: Subject to any disclaimer, the term of this patent is extended or adjusted under 35 U.S.C. 154(b) by 0 days.

(21) Appl. No.: 09/526,189

(22) Filed: Mar. 15, 2000

Related U.S. Application Data

(60) Provisional application No. 60/129,587, filed on Apr. 16, 1999, and provisional application No. 60/149,774, filed on Aug. 19, 1999.

(51) Int. Cl.⁷ .................................................. A61B 17/58
(52) U.S. Cl. .................. 606/61; 606/69; 606/72
(58) Field of Search .................. 606/60, 61, 69, 606/70, 71, 72

(56) References Cited

U.S. PATENT DOCUMENTS

| | | | |
|---|---|---|---|
| 2,443,363 | * 6/1948 | Townsend et al. | 606/69 |
| 5,084,048 | * 1/1992 | Jacob et al. | 606/61 |
| 5,209,751 | * 5/1993 | Farris et al. | 606/61 |
| 5,234,431 | 8/1993 | Keller . | |
| 5,261,910 | 11/1993 | Warden et al. . | |
| 5,304,179 | 4/1994 | Wagner . | |
| 5,531,745 | * 7/1996 | Ray | 606/61 |
| 5,545,163 | * 8/1996 | Miller et al. | 606/61 |
| 5,591,166 | 1/1997 | Bernhardt et al. . | |
| 5,601,553 | 2/1997 | Trebing et al. . | |
| 5,603,713 | 2/1997 | Aust et al. . | |
| 5,613,967 | 3/1997 | Englehardt et al. . | |
| 5,735,853 | 4/1998 | Olerud . | |
| 5,797,912 | 8/1998 | Runciman et al. . | |
| 5,810,823 | 9/1998 | Klaue et al. . | |
| 5,885,286 | 3/1999 | Sherman et al. . | |
| 6,066,140 | * 5/2000 | Gertzbein et al. | 606/61 |

FOREIGN PATENT DOCUMENTS 2 758 971 A1   8/1998   (FR) .

* cited by examiner

*Primary Examiner*—Gene Mancene
*Assistant Examiner*—Eduardo C. Robert
(74) *Attorney, Agent, or Firm*—Woodard, Emhardt, Naughton Moriarty & McNett

(57) ABSTRACT

A spinal implant system is disclosed for the fixation of bone segments in the spine. The system includes an elongated member, one or more bone anchor assemblies, and stabilizer members which are fitted within the elongated member. A bone anchor is attached to a bone, and the elongated member and stabilizer are fitted over the bone anchor. A rounded washer and nut having a corresponding rounded underside surface are fitted on to the bone anchor over the elongated member, and tightened. The configuration of the bone anchor assembly, including an intermediate portion of the bone anchor, the arcuate washer, and the nut, along with the configuration of the sliding support, allows multi-axial positioning of the bone anchor with respect to the elongated member at a plurality of locations along a slotted member.

34 Claims, 17 Drawing Sheets

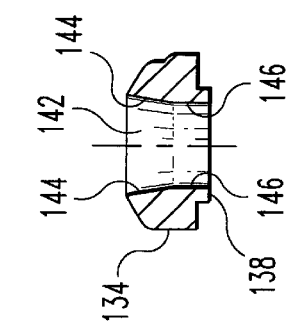
Fig. 9d
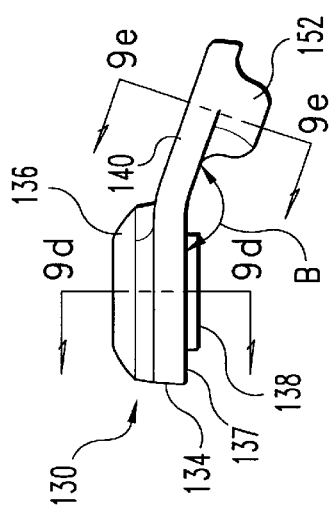
Fig. 9b
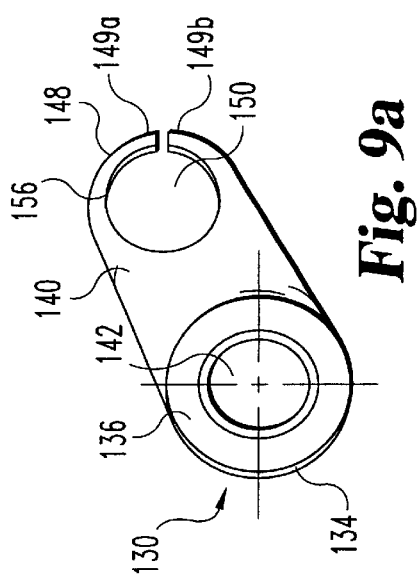
Fig. 9a
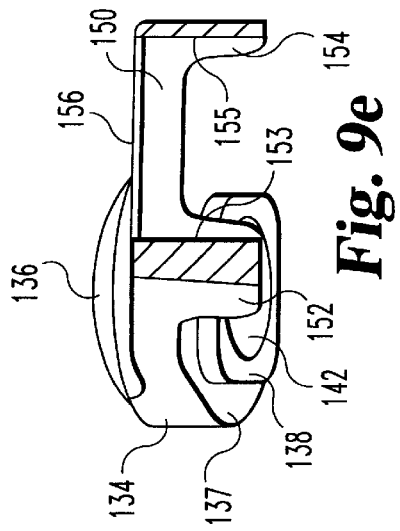
Fig. 9f
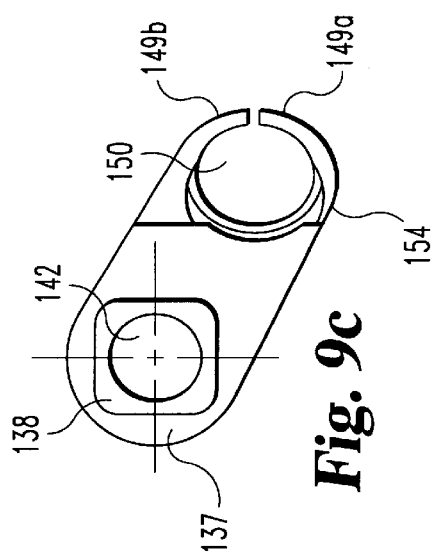
Fig. 9e
Fig. 9c

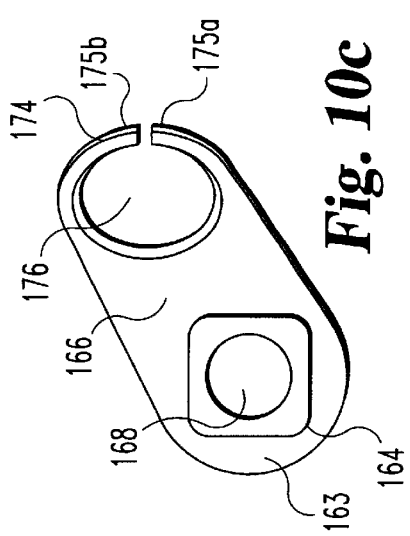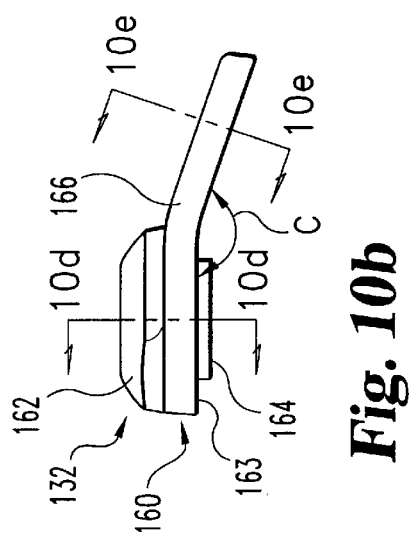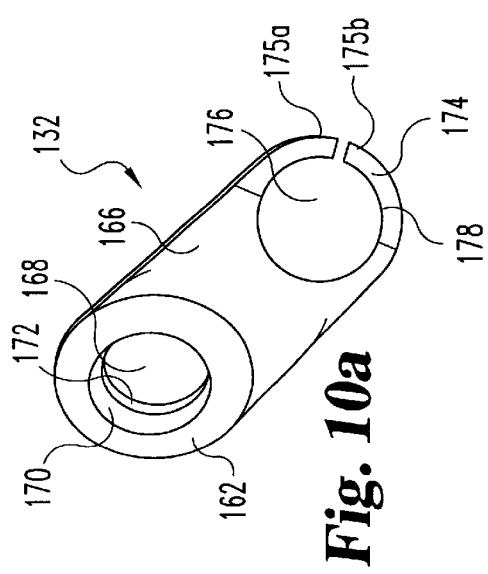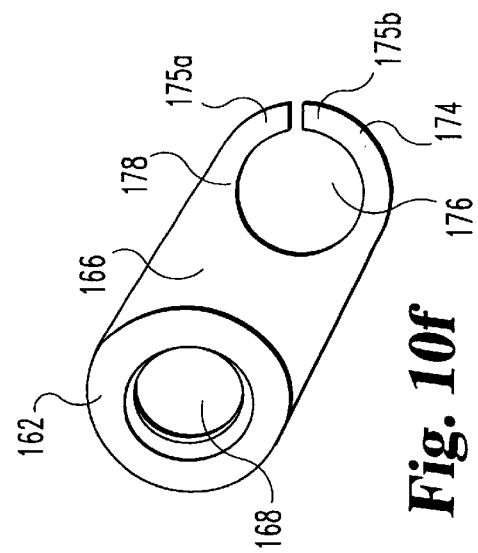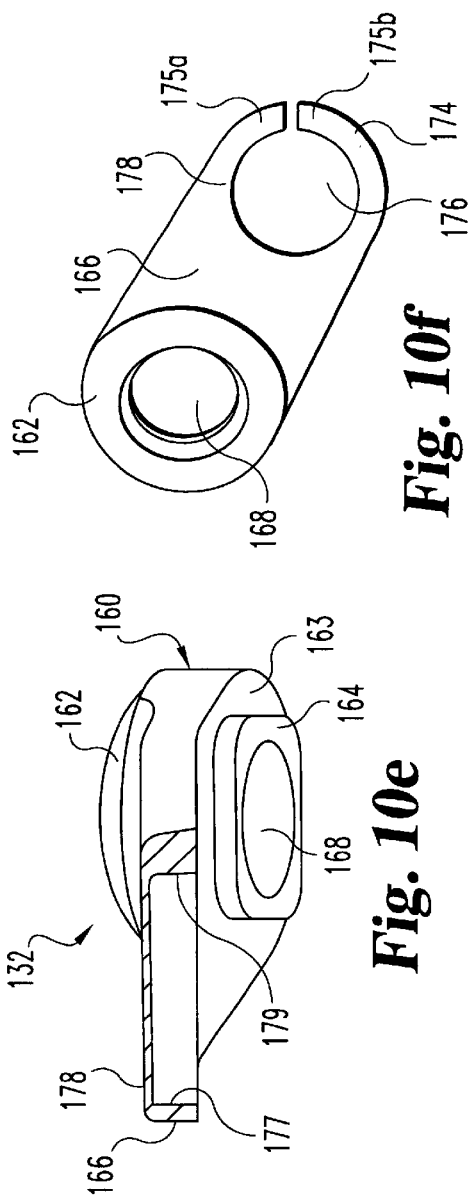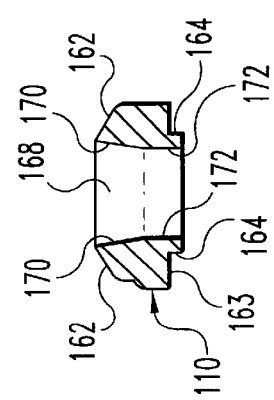
Fig. 10c
Fig. 10f
Fig. 10b
Fig. 10e
Fig. 10a
Fig. 10d

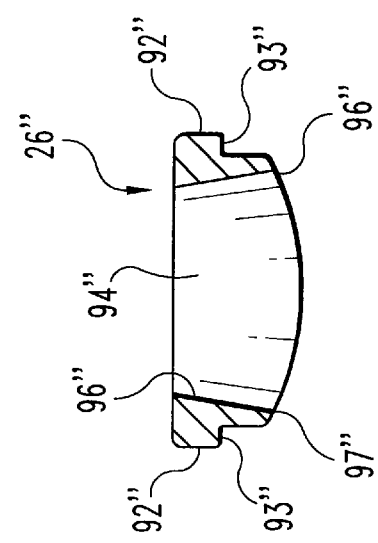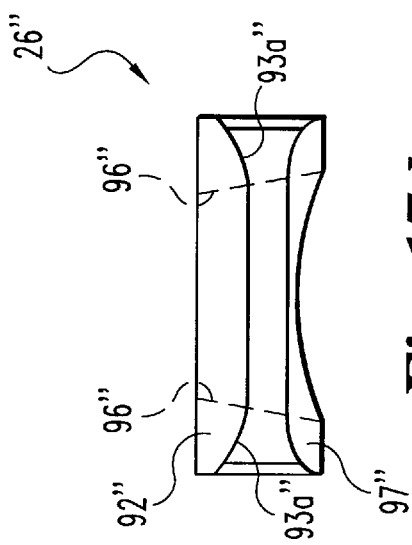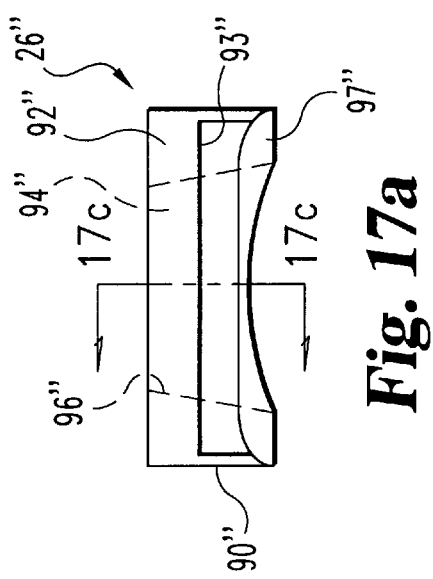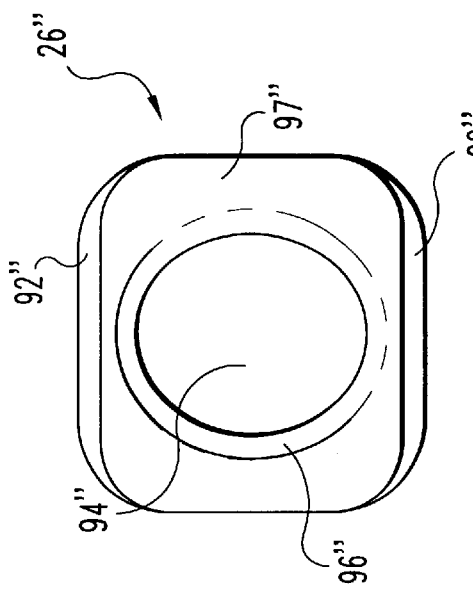

MULTI-AXIAL BONE ANCHOR SYSTEM

This application claims the benefit of U.S. Provisional Application Ser. No. 60/129,587, filed Apr. 16, 1999, and U.S. Provisional Application Ser. No. 60/149,774, filed Aug. 19, 1999.

FIELD OF THE INVENTION

The present invention concerns orthopedic implants, particularly for the spine or long bones. Specifically, the present invention includes a bone anchor system having multi-axial capabilities, which may be used in conjunction with an orthopedic implant device such as a spinal plate or rod system.

BACKGROUND OF THE INVENTION

In the art of orthopedic surgery, and particularly in spinal surgery, it has long been known to affix an elongated member, such as a plate or rod, to bones in order to hold them and support them in a given position. For example, in a procedure to fuse damaged vertebrae, the vertebrae are positioned in a corrected position as required by the surgeon. A plate is placed adjacent to the bone, and bone anchors are employed to secure the plate to the bones. Bone screws or bolts are commonly utilized as the bone anchors, and with such anchors placement is accomplished by drilling one or more holes in the bone(s), and threading the anchors into the holes. An example of a prior art bone bolt is described in a book by Dr. Cotrel entitled *New Instrumentation for Surgery of the Spine.* Freund, London 1986. This bone bolt is shown in FIG. 1. An anchor can be threaded into a hole through the plate, or the plate can be placed in position around the anchor after threading into the hole. The anchor and plate are then secured to each other to prevent relative movement. In this way, bones may be held and/or supported in proper alignment for healing.

A spinal plate system or other similar implant system may have anchors that can be positioned at a number of angles with respect to the plate or other implant. Such a feature allows easier placement of implant systems or correction of positioning of an implant system, in that the bone anchors need not be precisely positioned in angular relation with respect to the implant. Rather, with a multi-axial capability, holes can be drilled in a bone at a convenient location and/or angle, for example, and screws can be inserted therein, with the connection between the plate and the anchor being angularly adjustable to provide sufficient force perpendicular to the plate/bone interface to secure the plate.

The plate system disclosed in U.S. Pat. No. 5,613,967 to Engelhardt, et al., discloses a slotted plate through which a bone screw extends. The screw includes cancellous threads for placement in bone, an intermediate section with an upper flat portion, and a machine-threaded section. The machine-threaded portion fits through the slot in the plate, and the plate abuts the flat portion of the screw or a flat washer imposed between the intermediate portion of the screw and the plate. A bracket is placed over the machine-threaded portion of the screw and the slotted plate, and a nut is threaded on the machine-threaded portion of the screw to anchor the screw and plate together. This apparatus does not provide the preferred multi-axial capability, as described above.

U.S. Pat. No. 5,084,048 to Jacob et al., discloses apparatus for clamping a rod to a bone screw such that the longitudinal planes of the rod and screw are not perpendicular.

SUMMARY OF THE INVENTION

It is therefore an object of this invention to provide a spinal implant system having improved multi-axial capability and superior and strength and ease of use, particularly with respect to the spine.

Another object of the present invention is to provide a locking mechanism having a plurality of locking locations along a slotted member.

Still a further object of the present invention is in a preferred embodiment to provide an improved spine system with multi-axial capability and a plurality of locking locations along the systems.

Other objects will be evident from the following specification.

DESCRIPTION OF THE DRAWINGS

FIG. 4b is a cross sectional view of the embodiment of the orthopedic plate illustrated in FIG. 4a, taken along the lines 4b—4b in FIG. 4a.

FIG. 4d is a side view of the embodiment of the orthopedic plate illustrated in FIG. 4a.

FIG. 5b is a bottom view of the embodiment of the washer illustrated in FIG. 3a.

FIG. 5c is a sectional view of the embodiment of the washer illustrated in FIG. 3a.

FIG. 6b is a bottom view of the embodiment of the break-off nut illustrated in FIG. 4a.

FIG. 6c is a sectional view of the embodiment of the break-off nut illustrated in FIG. 4a.

FIG. 8b is a cross-sectional view, taken along the lines 8b—8b in FIG. 8a and viewed in the direction of the arrows, of the embodiment of the orthopedic plate illustrated in FIG. 8a.

FIG. 8c is a cross-sectional view, taken along the lines of 8c—8c in FIG. 8a and viewed in the direction of the arrows, of the embodiment of the orthopedic plate illustrated in FIG. 8a.

FIG. 8d is an end view of the superior end of the embodiment of the orthopedic plate illustrated in FIG. 8a.

FIG. 8e is a bottom view of the embodiment of the orthopedic plate illustrated in FIG. 8a.

FIG. 9a is a top view of an embodiment of a washer according to the present invention, viewed coaxially with a body portion of the washer.

FIG. 9b is a side view of the embodiment of the washer illustrated in FIG. 9a.

FIG. 9c is a bottom view of the embodiment of the washer illustrated in FIG. 9a.

FIG. 9d is a cross-sectional view, taken along the lines 9d—9d of FIG. 9b and viewed in the direction of the arrows, of the embodiment of the washer illustrated in FIG. 9a.

FIG. 9e is a cross-sectional view, taken along the lines 9e—9e of FIG. 9b and viewed in the direction of the arrows, of the embodiment of the washer illustrated in FIG. 9a.

FIG. 9f is a top view of the embodiment of the washer illustrated in FIG. 9a, viewed coaxially with an extension part of the washer.

FIG. 10a is a top view of an embodiment of a washer according to the present invention, viewed coaxially with a body portion of the washer.

FIG. 10b is a side view of the embodiment of the washer illustrated in FIG. 10a.

FIG. 10c is a bottom view of the embodiment of the washer illustrated in FIG. 10a.

FIG. 10d is a cross-sectional view, taken along the lines 10d—10d of FIG. 10b and viewed in the direction of the arrows, of the embodiment of the washer illustrated in FIG. 10a.

FIG. 10e is a cross-sectional view, taken along the lines 10e—10e of FIG. 10b and viewed in the direction of the arrows, of the embodiment of the washer illustrated in FIG. 10a.

FIG. 10f is a top view of the embodiment of the washer illustrated in FIG. 9a, viewed coaxially with an extension part of the washer.

FIG. 11b is a side view of another embodiment of the bone bolt illustrated in FIG. 11a.

FIG. 11c is a side view of another embodiment of the bone bolt illustrated in FIG. 11a.

FIG. 11d is a side view of another embodiment of the bone bolt illustrated in FIG. 11a.

FIG. 13b is a side view of the embodiment of the nut illustrated in FIG. 13a.

FIG. 13c is a cross-sectional view taken along the lines of 13c—13c and viewed in the direction of the arrows, of the embodiment of the nut illustrated in FIG. 13a.

FIG. 14b is a side view of the embodiment of the rod-bolt connector illustrated in FIG. 14a.

FIG. 14c is a cross-sectional view, taken along the lines 14c—14c of FIG. 14a and viewed in the direction of the arrows, of the embodiment of the rod-bolt connector illustrated in FIG. 14a.

FIG. 14d is a cross-sectional view, taken along the lines 14d—14d of FIG. 14a and viewed in the direction of the arrows, of the embodiment of the rod-bolt connector illustrated in FIG. 14a.

FIG. 15b is a cross-sectional view, taken along the lines 15b—15b of FIG. 15a and viewed in the direction of the arrows, of the embodiments of the rod-bolt connector, bone bolt, washer, nut and stabilizer illustrated in FIG. 15a.

FIG. 16b is a side elevational view of the embodiment of the stabilizer illustrated in FIG. 16a.

FIG. 16c is a cross-sectional view, taken along the lines 16c—16c of FIG. 16b and viewed in the direction of the arrows, of the embodiment of the stabilizer illustrated in FIG. 16a.

FIG. 17a is a side elevational view of a third embodiment of the stabilizer of the present invention.

FIG. 17b is a bottom view of the embodiment of the stabilizer illustrated in FIG. 17a.

FIG. 17c is a cross-sectional view, taken along the line 17c—17c of FIG. 17a and viewed in the direction of the arrows, of the embodiment of the stabilizer illustrated in FIG. 17a.

FIG. 17d is a side elevational view of a second version of the embodiment of the stabilizer illustrated in FIG. 17a.

DESCRIPTION OF THE PREFERRED EMBODIMENT

Figure 1:
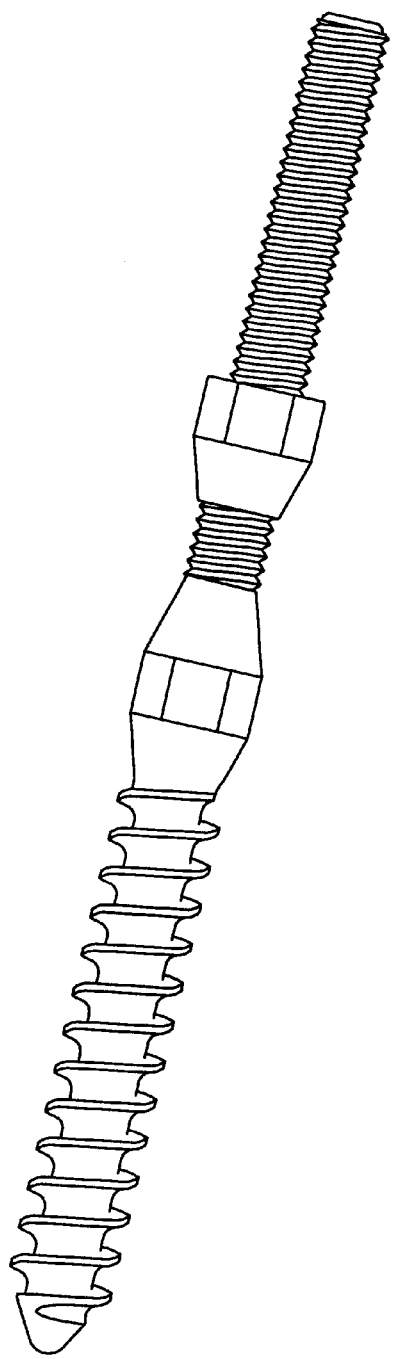
FIG. 1 is an illustration of a bone bolt used in a prior art spinal implant system.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein, being contemplated as would normally occur to one skilled in the art to which the invention relates.

Figure 2:
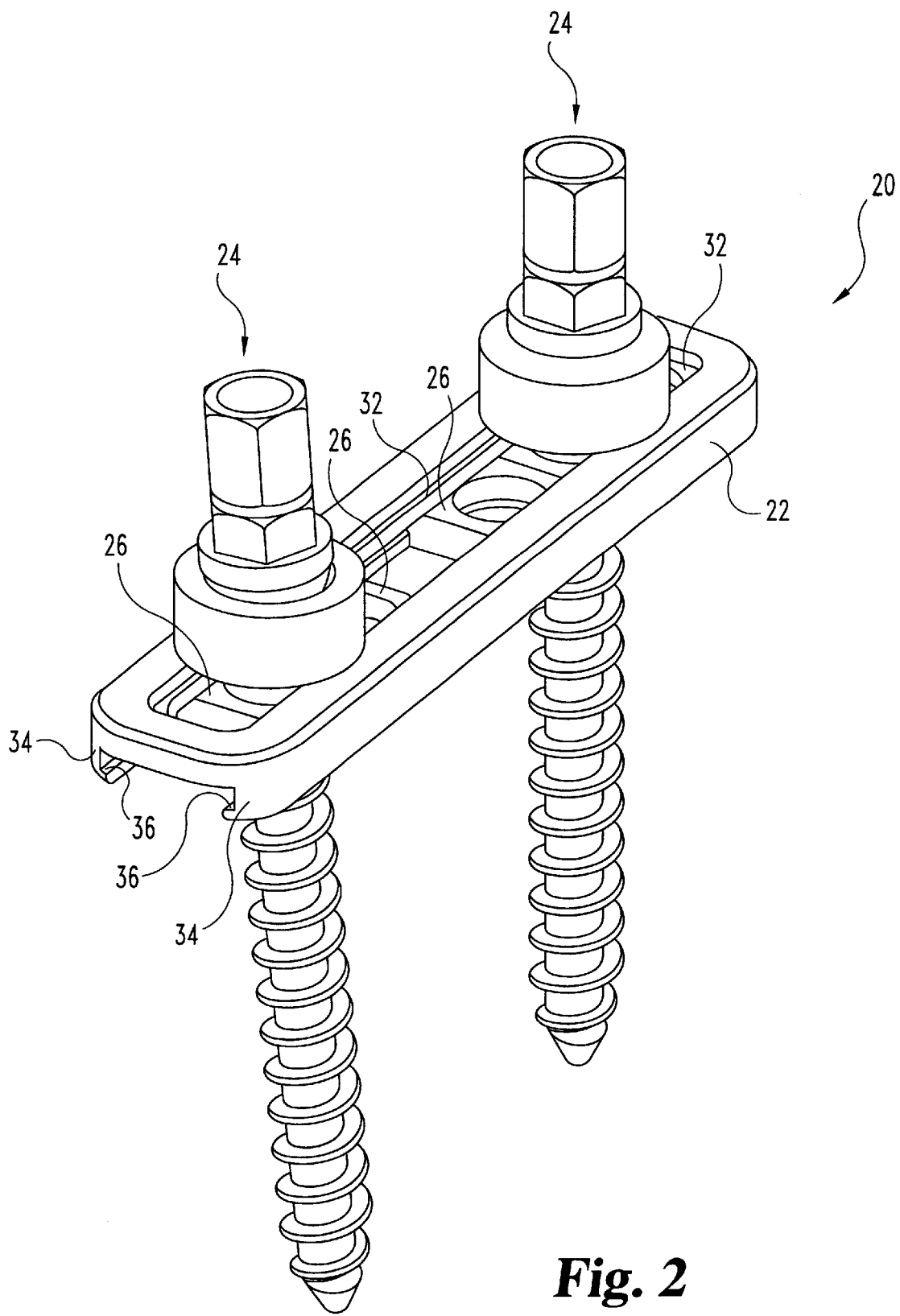
FIG. 2 is a perspective view of one embodiment of the system of the present invention.

Referring generally to FIG. 2, one embodiment of an orthopedic implant system 20 according to the present invention is illustrated. In that embodiment, implant system 20 includes an elongated member 22, a pair of bone anchor assemblies 24, and a set of supports or stabilizers 26. Differing numbers of any of those elements may be utilized without departing from the scope of this invention. For example, a plurality of elongated members 22 can be used in conjunction with each other, or a greater or lesser number of bone anchor assemblies 24 or stabilizers 26 may be used, depending upon the configuration of the elongated member, the medical problem to be addressed, and/or any other factors. The present invention contemplates at least one elongated member 22, at least one bone anchor assembly 24 and at least one stabilizer 26. Additionally, the non-provisional United States patent application entitled "Multi-Axial Bone Anchor System," filed on Mar. 15, 2000 in the name of the inventors of the present application, is hereby incorporated by reference into the present application as though it were fully set forth herein.

Referring now generally to FIGS. 4a–4e, there is shown an embodiment of elongated member 22 according to the present invention. Elongated member 22 is in the form of a generally rectangular flat plate and includes a generally longitudinal slot 30 through the thickness of elongated member 22. Within slot 30 is formed a ledge 32. Elongated member 22 also includes a pair of downwardly-extending arms 34 substantially along the length of both sides of elongated member 22. Arms 34 have an inwardly-extending ledge 36 along substantially the entire length of arms 34.

Referring now generally to FIGS. 2–7, there is shown one preferred embodiment of the bone anchor assembly 24 of the present invention. Generally, bone anchor assembly 24 includes a bone bolt 40, an arcuate washer 42, and a break-off nut 44. In the illustrated embodiment, bone bolt 40 includes a bone-engaging portion 46 having cancellous threads 48 thereon. Bone bolt 40 also includes a proximal portion 50, which is threaded with machine threads. Between proximal portion 50 and bone-engaging portion 46, there is an intermediate portion 54 which has a rounded configuration. In one specific embodiment, the rounded shoulder has a spherical configuration. The bone bolt is more specifically described below.

Figure 5A:
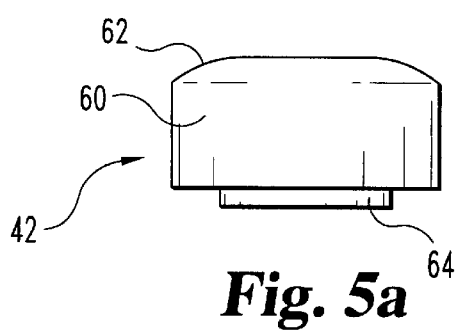
FIG. 5a is a side elevational view of one embodiment of a washer used in the embodiment of the invention illustrated in FIG. 1.
Figure 5C:
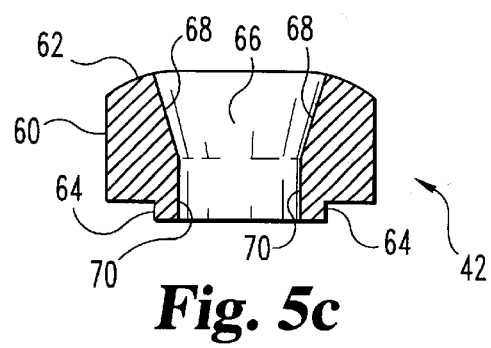
Figure 5B:
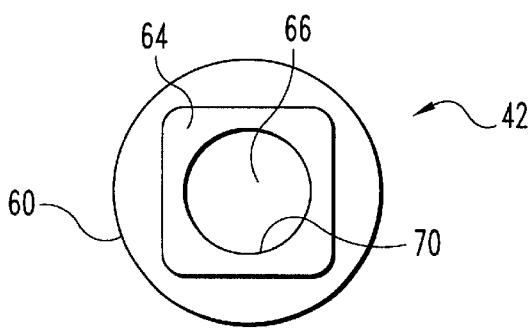
Figure 6A:
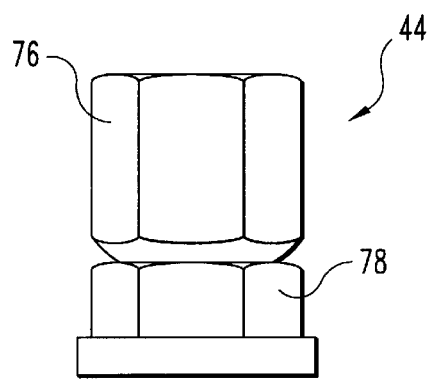
FIG. 6a is a side elevational view of one embodiment of a break-off nut as used in the embodiment of the invention illustrated in FIG. 1.
Figure 6C:
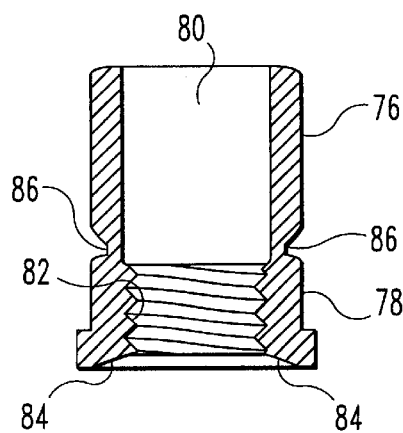
Figure 6B:
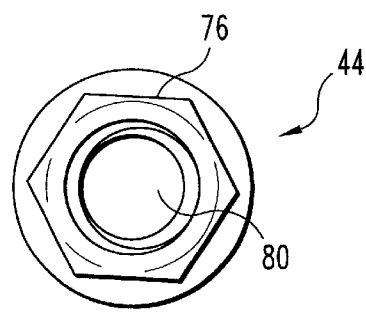

Referring generally to FIGS. 5a–5c, arcuate washer 42 of bone anchor assembly 24 has a generally cylindrical body 60, a rounded or conical head 62, a underside projection 64, and an aperture 66 therethrough. Aperture 66 is bounded by inner walls 68 and 70 of washer 42. In the illustrated embodiment, inner wall 68 is conical or tapered such that aperture 66 decreases in diameter from head 62 toward body 60, and inner wall 70 is substantially cylindrical. Alternate configurations of walls 68 and 70 are considered to be within the scope of the present invention. For example, inner wall 70 may not be contiguous with inner wall 68, or walls 68 and 70 may form a single conical surface bounding aperture 66. Projection 64 also bounds aperture 66, and in a specific embodiment the outer dimension of projection 64 is approximately square and sized to fit within slot 30 and atop ledge 32 of elongated member 22.

Further included in bone anchor assembly 24 is a break-off nut 44. As shown more clearly in FIGS. 6a–6c, break-off nut 44 includes an upper break-off portion 76 and a nut portion 78. Both break-off portion 76 and nut portion 78 preferably have a hexagonal outer shape, although any known configuration of the outer portion of break-off portion 76 and nut portion 78 that will allow transmission of torque to one or both can be used with the present invention.

Figure 7A:
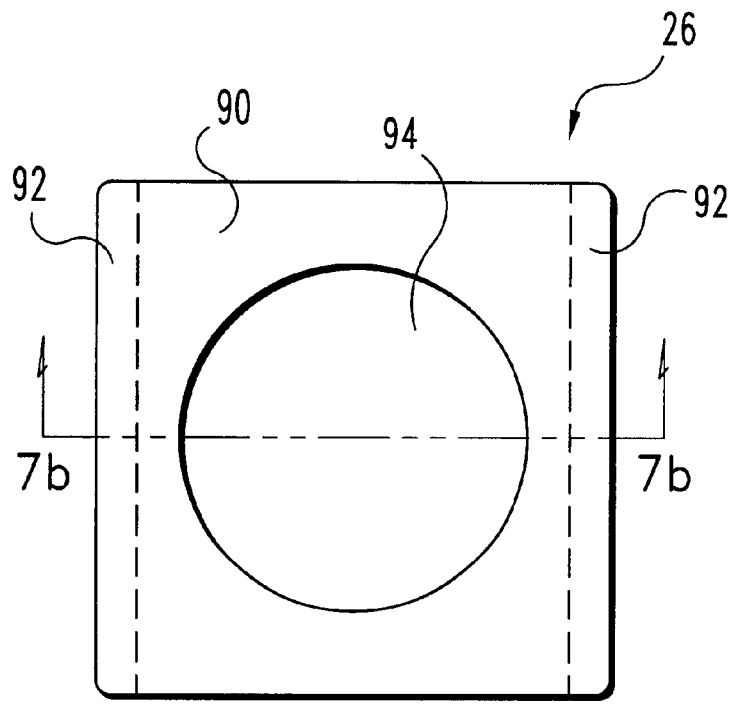
FIG. 7a is a top view of one embodiment of the stabilizer used in the embodiment of the invention illustrated in FIG. 1.
Figure 7B:
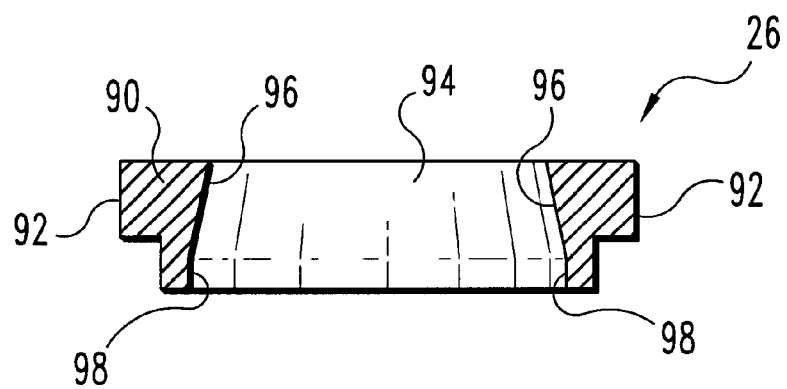
FIG. 7b is a cross section of the embodiment of the stabilizer illustrated in FIG. 5a, taken along the direction of the arrows.
Figure 8B:
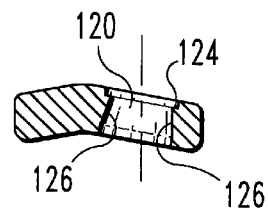
Figure 8A:
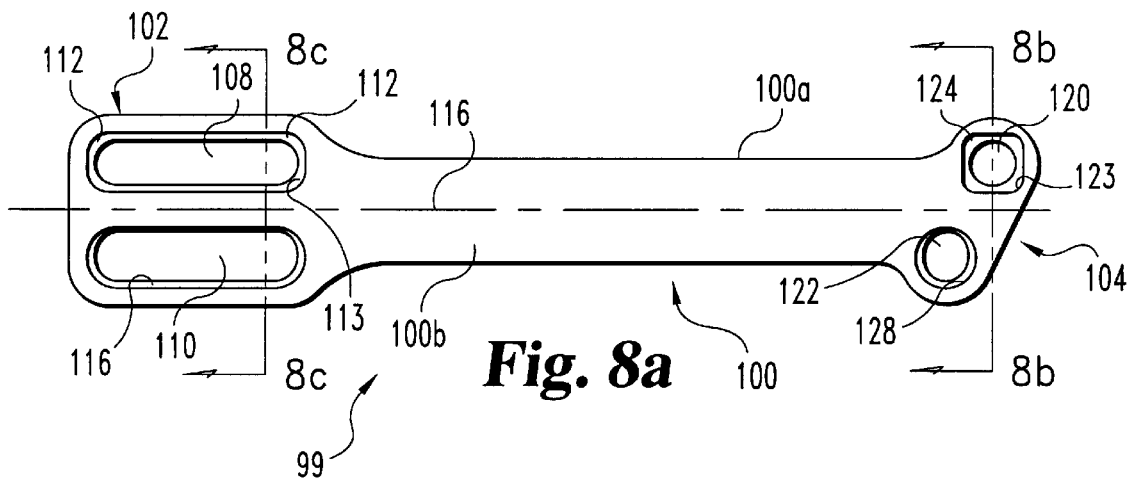
FIG. 8a is a top view of an alternate embodiment of an orthopedic plate according to the present invention.
Figure 8C:
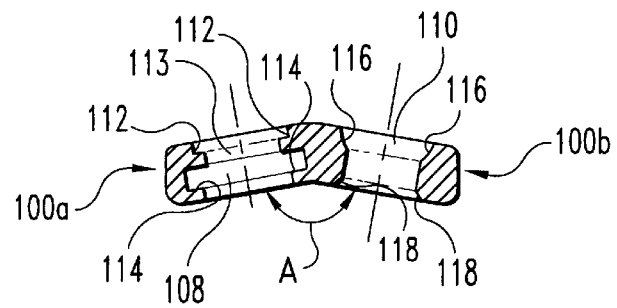
Figure 8D:
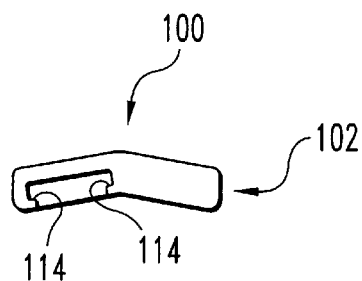
Figure 8E:
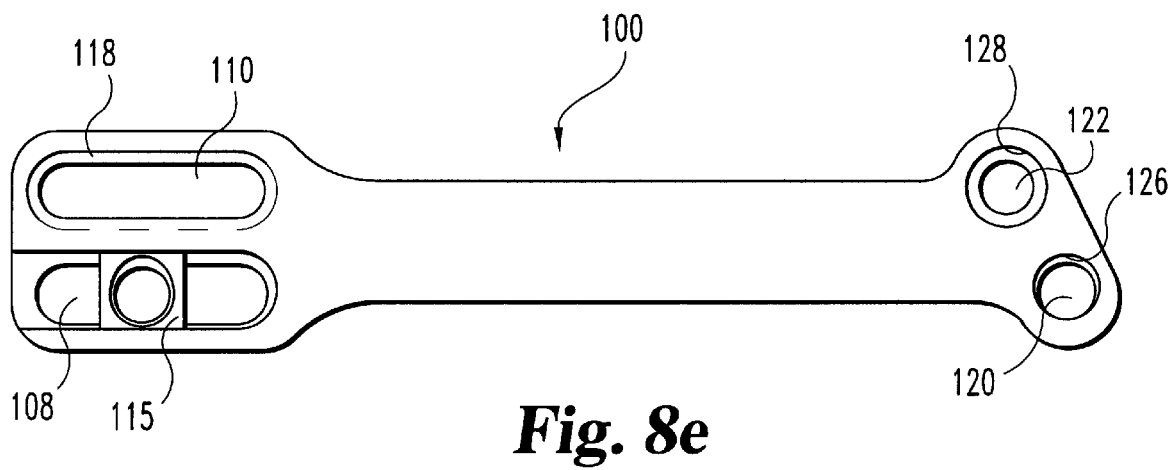

Break-off nut 44 includes a longitudinal bore 80 therethrough. Bore 80, in a specific embodiment, is substantially cylindrical within break-off portion 76, and is substantially cylindrical with a female thread 82 within nut portion 78. Approaching the bottom end of nut portion 78, bore 80 is bounded by a surface 84 for complementary mating with head 62 of arcuate washer 42. While it is contemplated that the surfaces may have any configuration, in a preferred embodiment surface 84 is generally spherical, having a radius larger than the radius of bore 80, and substantially the same radius as the generally spherical head 62 of washer 42. Break-off nut 44 also includes a groove or weakened area 86 that allows shearing separation of break-off portion 76 from nut portion 78 after break-off nut 44 has been tightened sufficiently. Also included in implant system 20 are one or more stabilizers or supports 26 (FIGS. 7a and 7b). Stabilizer 26, in one embodiment, has an approximately square body 90 with an extending finger portion 92 on opposite sides of stabilizer 26. Stabilizer 26 also has a bore 94 therethrough. Bore 94 is bounded by a conical or tapered wall 96 and substantially cylindrical wall 98. Alternative configurations of walls 96 and 98 are contemplated as being within the scope of the present invention. For example, walls 96 and 98 could be non-contiguous or walls 96 and 98 could form a single conical wall bounding bore 94. Fingers 92 of stabilizer 26 are shaped and dimensioned to fit within slot 39 of elongated member 22 such that fingers 92 abut ledges 36 and undersurface 37 of elongated member 22. In this embodiment, stabilizer 26 has a substantially flat bottom surface 97. One or more stabilizers 26 may be inserted into slot 39 via an open end of elongated member 22, and until implant system 20 is finally tightened or locked as described below, are slidable along ledges 36 of elongated member 22.

Figure 16A:
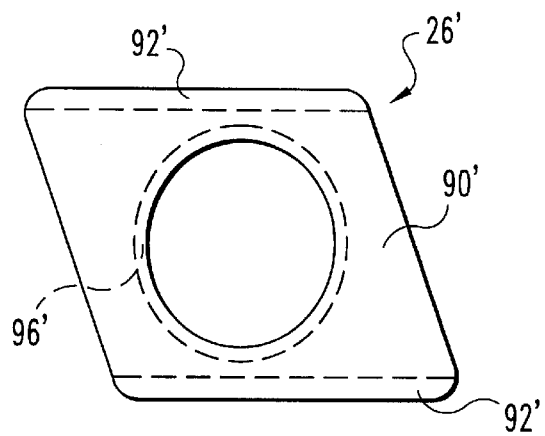
FIG. 16a is a top view of a second embodiment of the stabilizer of the present invention.
Figure 16B:
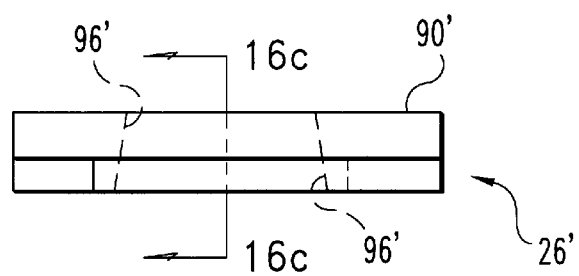
Figure 16C:
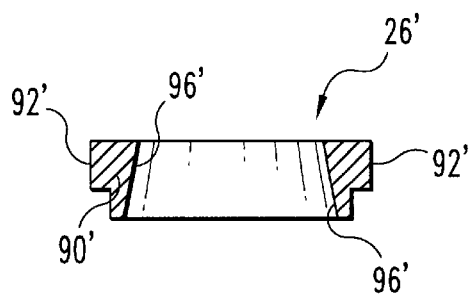

A second embodiment of stabilizer 26' is illustrated in FIGS. 16a–16c. Stabilizer 26' is like stabilizer 26 in most respects. However, stabilizer 26' has a body 90' approximately in the shape of a parallelogram. Finger portions 92', bore 94' and tapered wall 96' are substantially similar to finger portions 92, bore 94, and tapered wall 96 of stabilizer 26, described and illustrated above. As noted above, alternative configurations of the walls of bore 94' are contemplated as being within the scope of the present invention. For example, tapered wall 96' could be contiguous with or separate from a cylindrical wall which also bounds bore 94'. Fingers 92' are shaped in dimension to fit within slot 39 of elongated member 22 such that FIGS. 92' abut ledges 36 and under surface 37 of elongated member 22. One or more stabilizers 26' may be inserted into slot 39 via an open end of elongated member 22, and until implant system 20 is finally tightened or locked as described below, are slideable along ledges 36 of elongated member 22. The parallelogram configuration of stabilizer 26' allows close center line-to-center line placement of bone bolts or screws when multiple stabilizers 26' are placed adjacent each other, and can reduce the overall thickness of the plate and stabilizer combination required for successful fixation.

In a third embodiment, stabilizer 26" is depicted in FIGS. 17a–17c. Stabilizer 26" has an approximately rectangular body 90" with extending finger portions 92" on opposite sides of stabilizer 26". Finger portions 92", like finger portions 92 and 92', have flat undersides 93" in one embodiment. Alternatively, in another embodiment (FIG. 17d) finger portions 92" (and by extension, finger portions 92 and 92' of stabilizers 26 and 26') can have convexly rounded undersides 93a". Stabilizer 26" also has a bore 94" therethrough. Bore 94" is preferably bounded by a conical or tapered wall 96", although alternative configurations of wall 96" are contemplated as being within the scope of the present invention, as discussed above with reference to stabilizers 26 and 26'. Stabilizer 26" also includes a rounded bottom surface 97" that substantially surrounds the lower opening of bore 94". In one specific embodiment of stabilizer 26" rounded bottom 97" has a configuration of a portion of a cylinder. Fingers 92" of stabilizer 26" are shaped and dimensioned to fit within slot 39 of elongated member 22 such that fingers 92" abut ledges 36 and under surface 37 of elongated member 22. One or more stabilizers 26" may be inserted into slot 39 via an open end of elongated member 22, and until implant system 20 is finally tightened or locked as described below, are slideable along ledges 36 of elongated member 22. While the description below specifically names only stabilizer 26, it is understood that stabilizers 26' and 26" are used in the same manner.

Figure 3:
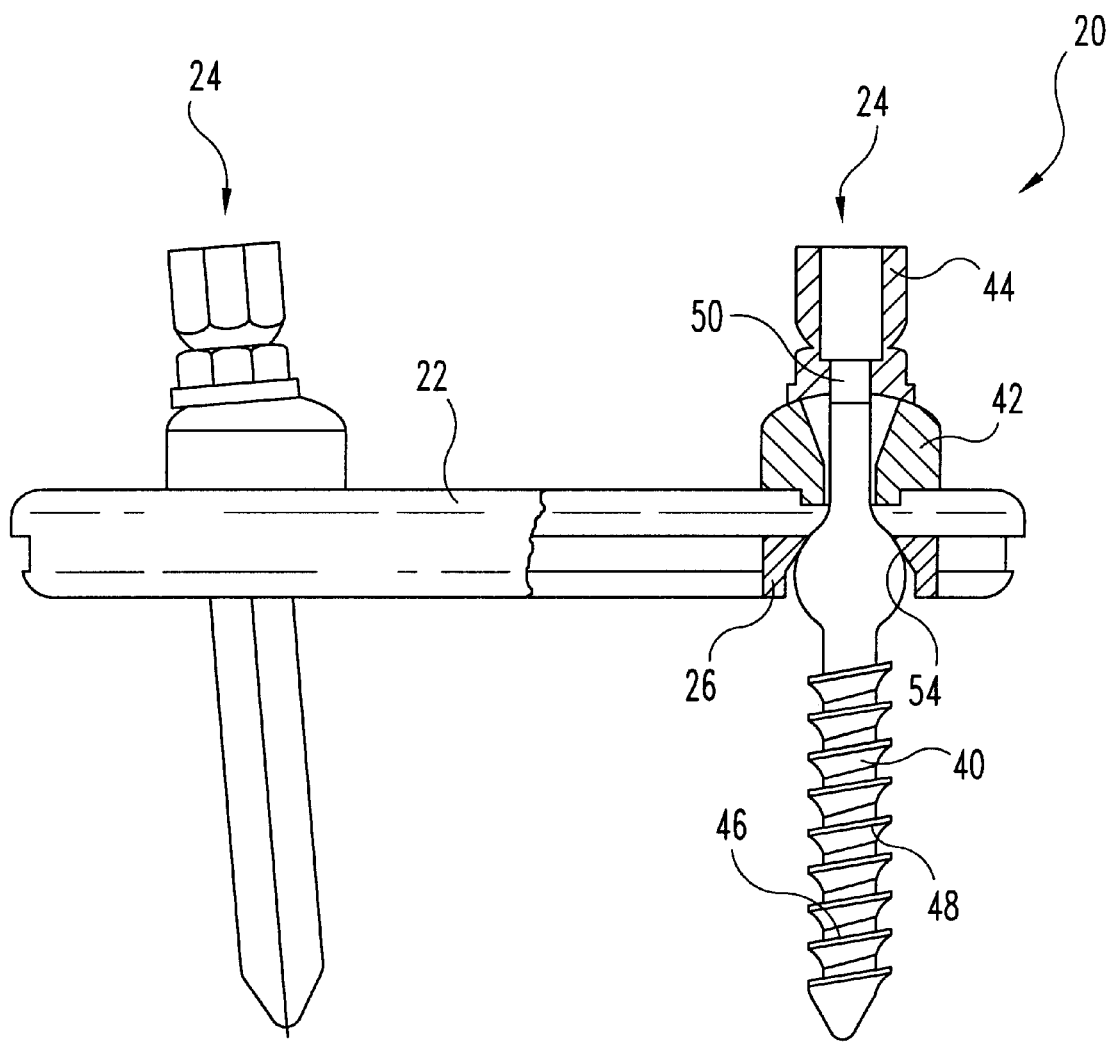
FIG. 3 is a partial sectional view of the embodiment of the invention illustrated in FIG. 1.
Figure 4A:
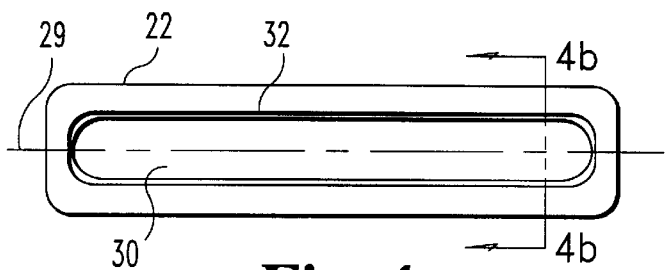
FIG. 4a is a top view of one embodiment of an orthopedic plate used with the embodiment of the invention illustrated in FIG. 1.
Figure 4B:
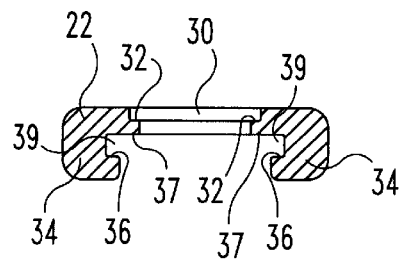
Figure 4C:
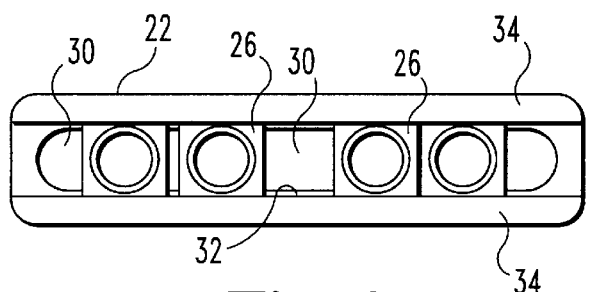
FIG. 4c is a bottom view of the embodiment of the orthopedic plate illustrated in FIG. 4a, including a set of stabilizers according to the embodiment illustrated in FIGS. 7a and 7b.
Figure 4D:
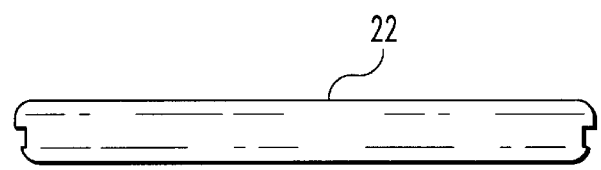
Figure 4E:
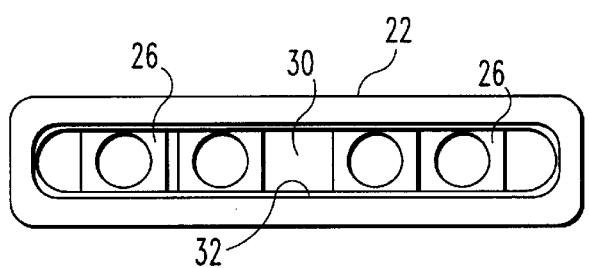
FIG. 4e is a top view of the embodiment of the orthopedic plate along with stabilizers as illustrated in FIG. 4c.

Referring now generally to FIGS. 2 and 3, implant system 20 is assembled and used as follows. After the surgeon has drilled one or more holes into a bone or bones, bone bolt 40 is threaded into the hole via cancellous threads on bone-engaging portion 46. After bone bolt 40 is securely affixed to the bone, elongated member 22 including a fitted support or stabilizer 26 is placed over bone bolt 40, so that proximal portion 50 of bone bolt 40 extends through bore 94 of stabilizer 26 and slot 30 of elongated member 22, and such that intermediate portion 54 of bone bolt 40 is within or adjacent to bore 94 of stabilizer 26. Washer 42 is placed over proximal portion 50 of bone bolt 40, so that proximal portion 50 extends through aperture 66 of washer 42, and so that underside surface 63 of washer 42 rests on elongated member 22 and underside projection 64 of washer 42 abuts ledge 32 within slot 30 of elongated member 22. In the embodiment in which projection 64 has an approximately square outer configuration, washer 42 will not be able to rotate about bone bolt 40 when projection 64 is within slot 30 of elongated member 22. When washer 42 is in place, break-off nut 44 is loosely threaded onto machine thread 52 of bone screw 40, such that surface 84 of nut portion 78 is in adjustable contact with or adjacent to head 62 of washer 42. Elongated member can then be adjusted with respect to bone bolt 40, and bone bolt 40 may thereby form one of a variety of angles with respect to elongated member 22. The rounded part 56 of intermediate portion 54 of bone bolt 40 is able to articulate within bore 94 and wall portion 96 of stabilizer 26, and inner wall 68 of washer 42 permits proximal portion 50 of bone bolt 40 to correspondingly occupy various angular positions with respect to washer 42 and elongated member 22.

After elongated member 22 is properly positioned with respect to bone bolt 40, break-off nut 44 is tightened. As break-off nut 44 is tightened, the torque on break-off portion 76 increases, until break-off portion 76 shears away from nut portion 78 at groove 86. Preferably, groove 86 is above the uppermost portion of bone screw 40 to inhibit irritation to surrounding tissue that might be caused by a protruding post. Surface 84 of nut portion 78, being configured similarly or identically to head 62 of washer 42, is able to matingly engage any portion of head 62, enabling secure, tight contact between nut portion 78 and washer 42 regardless of the angle between bone bolt 40 and elongated member 22.

An alternative embodiment 99 of the present invention is illustrated in FIGS. 8–13. Referring generally to FIG. 8, there is shown an elongated member 100 according to that alternative embodiment. Elongated member 100 includes a superior end 102, an inferior or caudal end 104, and a longitudinal axis 106 generally extending there between. Typically, when implanted superior end 102 and inferior end 104 will be oriented as cephalad and caudal ends, respectively.

Superior end 102 includes a pair of longitudinal slots 108 and 110, which are placed transversely of each other. Slot 108 has a configuration very similar to the arrangement of slot 30 in elongated member 22. Slot 108 includes a ledge 112 near the upper part of elongated 100, which substantially encircles slot 108 in one specific embodiment. It is contemplated that in another embodiment, slot 108 may include two ledges 112, each running along substantially the entire length of a longitudinal side of slot 108. Preferably, side walls 113, immediately adjacent ledges 112, form a rectangular configuration in the upper portion of slot 108. Slot 108 also has a lower ledge 114 that runs substantially along each longitudinal side of slot 108. A stabilizer 115 (similar to stabilizer 26 described above) may be placed to bear against ledge 114 as previously discussed with respect to the embodiment of FIG. 2. Slot 110 includes a first arcuate or conical surface 116 near the upper surface of elongated member 100, and a second arcuate or conical surface 118 near the lower surface of elongated member 100. In a specific embodiment, surfaces 116 and 118 are substantially circular in cross-section. In a preferred aspect, the radius of surface 118 is larger than that of surface 116.

Inferior end 104 of elongated member 100 includes a pair of bores 120 and 122. Bore 120 includes side walls 123 and a ledge 124 near the upper surface of elongated member of 100. Side walls 123 define a generally square opening. Bore 120 further includes wall 126 which tapers outward in a substantially conical shape from upper to lower surfaces of elongated member 100. Bore 122 is a substantially circular bore, having an arcuate surface 128 near the upper surface of elongated member 100. In a preferred embodiment, arcuate surface 128 is spherical.

Additionally, elongated member 100 includes a bend along axis 106, separating elongated member 100 into side portions 100a and 100b. Angle A between side portions 100a and 100b is approximately 163 degrees in a preferred embodiment. Other inside angles A of elongated member 100 are contemplated as within the scope of the present invention, as may be required by the configurations of the bones to which elongated member 100 is to be attached or other factors.

The embodiment of the implant system 99 incorporating elongated member 100 also includes superior or cephalad washer 130 and inferior or caudal washer 132. Referring to FIGS. 9a–f, superior washer 130 includes a body portion 134 having an conical or rounded head 136 and an underside 137 having a projection 138, and a lateral extension portion 140. In the illustrated embodiment of washer 130, head 136 forms a portion of a sphere, and underside projection 138 is flat and in the general form of a square with rounded corners, with the sides of the square of a size slightly less than the width of slot 108 of elongated member 100. An aperture 142 extends through body 134 of washer 130. An upper wall portion 144 bounds aperture 142, and is tapered from head 136 toward the bottom of washer 130. A lower wall portion 146 is generally cylindrical. However, other wall configurations are possible, for example, wall portions 144 and 146 may not be contiguous, or may form a single tapered wall from head 136 to projection 138.

Lateral extension portion 140 of washer 130 includes a C-clip portion 148, which encloses most of an aperture 150, and downwardly extending flanges 152 and 154. C-clip portion 148 has a pair of fingers 149a and 149b. Fingers 149a and 149b have a beveled or substantially conical projection 156 at their respective upper portions. The interior opening defined by projection 156 has a slightly smaller diameter than the interior opening defined by walls 153 and 155. Flanges 152 and 154, in a specific embodiment, have a length parallel to extension portion 140 slightly smaller than the width of slot 110 of elongated member 100. Washer 130 also includes a bend in lateral extension portion 140 that is complementary to the bend along longitudinal axis 106 of elongated member 100. The inside angle B formed by the bend in washer 130 is approximately the same as angle A of elongated member 100.

In use, washer 130 is fitted into slots 108 and 110 of elongated member 100. Specifically, body portion 134 is placed on slot 108 such that underside 137 of body portion 134 rests on elongated member 100 and projection 138 of body 134 is fitted into slot 108 and rests on ledge 112. Flanges 152 and 154 of extension portion 140 are fitted into slot 110. In this configuration, washer 130 cannot rotate with respect to elongated member 100 because of the respective fits between (a) projection 138 and the sides of slot 108, (b) flanges 152 and 154 and the sides of slot 110, and (c) the bend in both washer 130 and elongated member 100.

Referring now generally to FIGS. 10a–f, an embodiment of inferior washer 132 is illustrated. Washer 132 includes a body 160 having a conical or rounded head 162 and an underside 163 having a substantially square projection 164, and an extension 166. Body 160 has an aperture 168 extending therethrough, extending from head 162 to projection 164. Aperture 168 is bounded by wall sections 170 and 172. In a specific embodiment, wall section 170 is conically tapered from head 162 toward underside projection 164, and wall section 172 is substantially cylindrical. Other configurations are possible, however, such as wall sections 170 and 172 being non-contiguous or forming a single conically tapered surface.

Lateral extension 166 includes a C-clip portion 174, which encircles most of substantially cylindrical aperture 176. C-clip portion 174 has a pair of fingers 175a and 175b. Fingers 175b and 175b have a beveled or substantially conical projection 178 at their respective upper portions. The opening defined by projection 178 has a diameter slightly smaller than the diameter defined by walls 177 and 179. Washer 132 also includes a bend in lateral extension portion 166 that is complementary to the bend along longitudinal axis 106 of elongated member 100. The inside angle C formed by the bend in washer 132 is approximately the same as angle A of elongated member 100.

Referring generally to FIG. 11, there is shown a more detailed depiction of a form of bone bolt 200 which can be used with elongated member 100 or elongated member 22. Bone bolt 200 includes a bone-engaging portion 202, a proximal portion 204, and an intermediate portion 206. Preferably, bone-engaging portion 202 includes cancellous thread 208, which winds along the length of bone-engaging portion 202 until thread 208 adjoins intermediate portion 206. As the thread pattern nears intermediate portion 206, the root diameter of the thread increases.

Figure 11A:
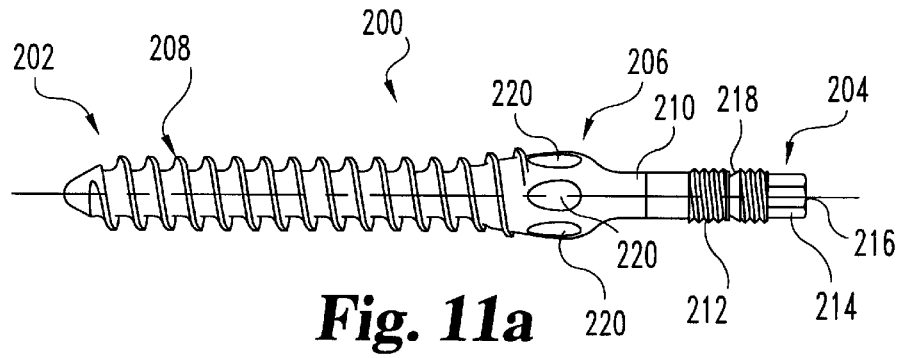
FIG. 11a is a side view is an embodiment of a bone bolt of the present invention.
Figure 11B:
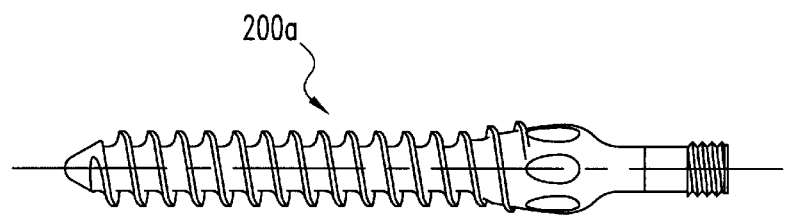
Figure 11C:
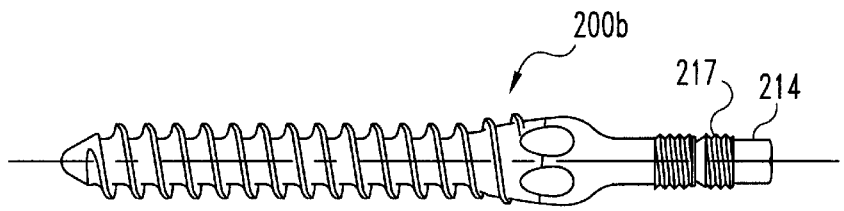
Figure 11D:
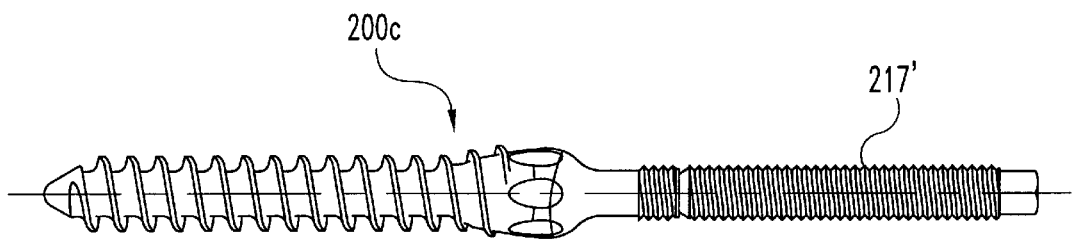

Proximal end 204 includes a shaft portion 210 adjoining intermediate portion 206, a threaded portion 212 proximal of shaft portion 210, and a break-off portion 214 proximal of threaded portion 212. In a specific embodiment, break off portion 214 includes torque applying surfaces 216 (for example, hexagonal outer surfaces) to be engaged by a wrench or other nut-driver, and a groove or weakened portion 218. When bolt 200 is secure, further torque applied to torque applying surfaces 216 will cause break-off portion 214 to shear from threaded portion 212 at groove or weakened portion 218. Break-off portion 214 is preferably configured so that shear occurs when a relatively light torque is applied, e.g. in the range of 10–11 newton-meters. Surface 216 may be used to prevent bolt rotation while the bolt is connected to an elongated member by a nut. Intermediate portion 206 of bolt 200 is generally rounded, and includes a set of flattened areas 220. In a specific embodiment, flattened areas 220 are uniformly spaced around the circumference of intermediate portion 206, in a hexagonal arrangement Other alternative embodiments of bone bolt 200 are within the scope of the present invention. Referring to FIGS. 11b–11d, there are illustrated bone bolts 200a, 200b and 200c. Bone bolt 200a includes the parts of bone bolt 200 identified above, but does not include break-off portion 214. Bone bolt 200b includes, in addition to the features of bone bolt 200, a machine threaded section 217 on break-off portion 214. Bone bolt 200c includes a longer machine threaded section 217'. Machine threads 217 and 217' may be used to enable the surgeon to shear off break-off portion 214 without losing break-off portion 214 or dropping it into the patient. Further, maching threads 217' have sufficient length to allow reduction of stripped vertebra. A cannulated tool having a female thread at its distal end and inner surfaces for torque application (e.g., hexagonal inner surfaces for engaging torque application surfaces 216 of break-off section 214) could be threaded onto machine threads 217 or 217', and the inner torque surfaces of the tool engaged with break-off portion 214. When break-off portion 214 is sheared from bolt 200b or 200c, break-off portion 214 is held by the tool by virtue of the interengaged female tool thread and machine threads 217 or 217' of break-off portion 214 of bolt 200b or 200c.

Figure 12:
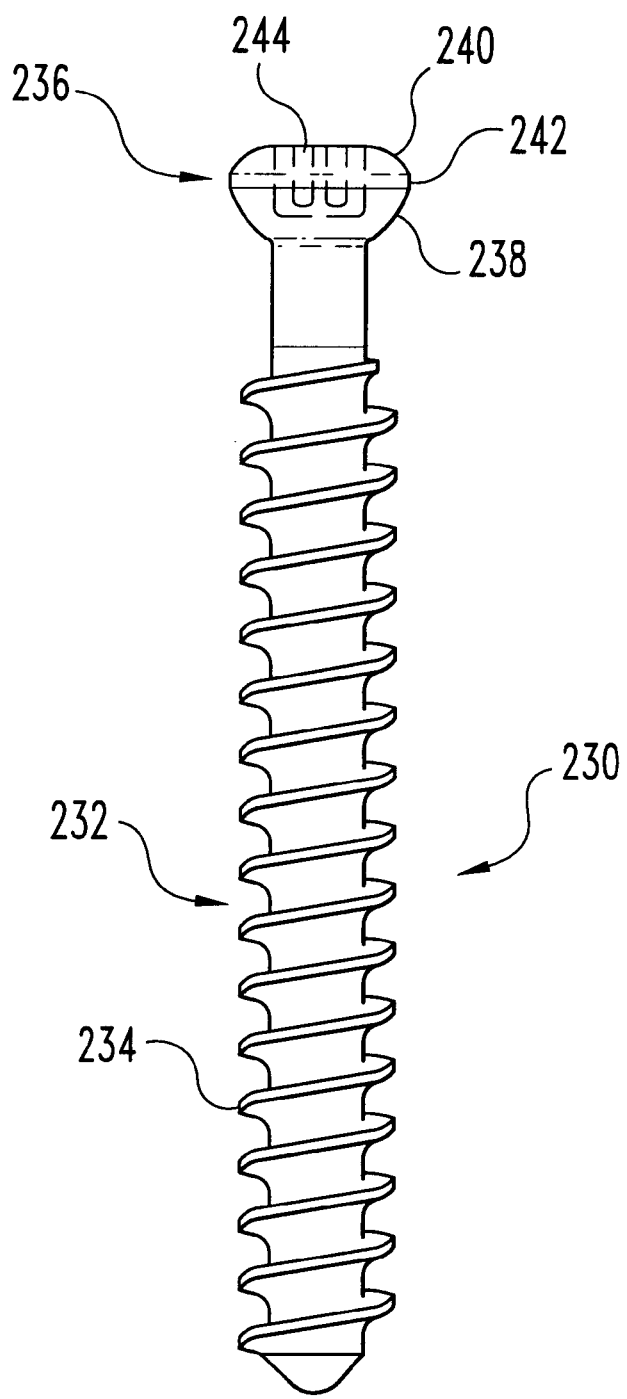
FIG. 12 is a side view of an embodiment of a bone screw for use with present invention.

Now referring generally to FIG. 12, there is illustrated bone screw 230 of the present invention. Bone screw 230 includes a bone engaging portion 232 having cancellous threads 243 thereon, and a head portion 236. Head portion 236 includes a lower rounded surface 248 and an upper rounded surface 240. In a specific embodiment, surfaces 238 and 240 are separated by a generally cylindrical portion 242. Head 236 also includes a tool-engaging recess 244. Tool-engaging recess 244 may be of any suitable configuration, including hexagonal, hexalobed, or other configuration.

Figure 13A:
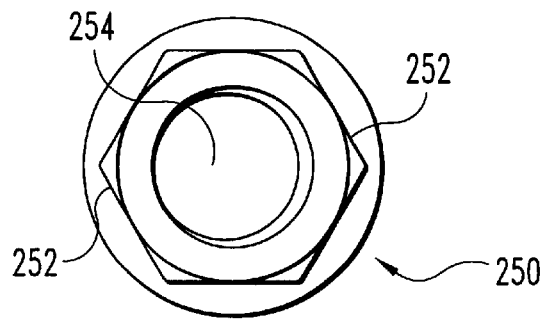
FIG. 13a is a top view of an embodiment of a nut for use with the present invention.
Figure 13B:
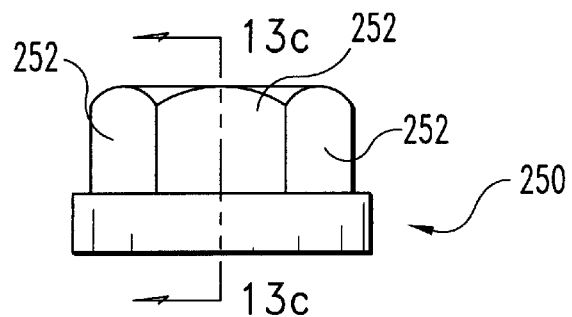
Figure 13C:
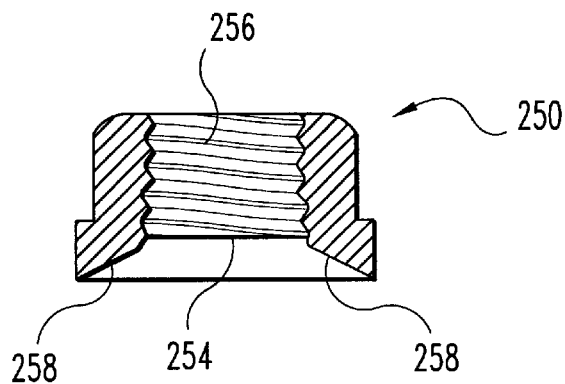
Figure 14A:
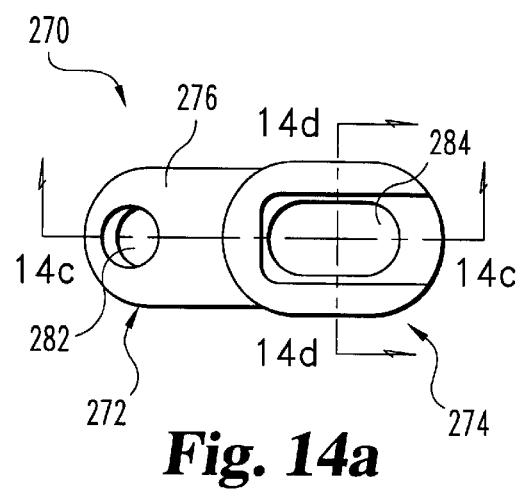
FIG. 14a is a top view of an embodiment of a rod-bolt connector for use with the present invention.
Figure 14C:
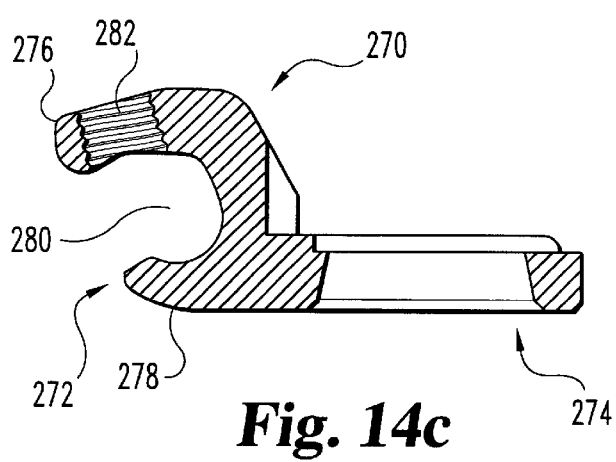
Figure 14B:
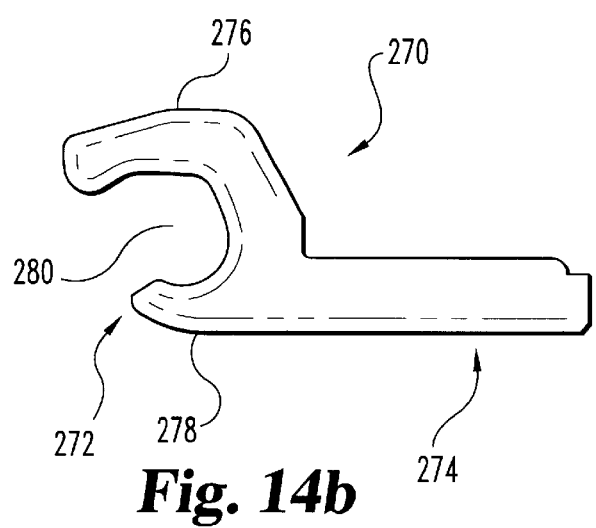
Figure 14D:
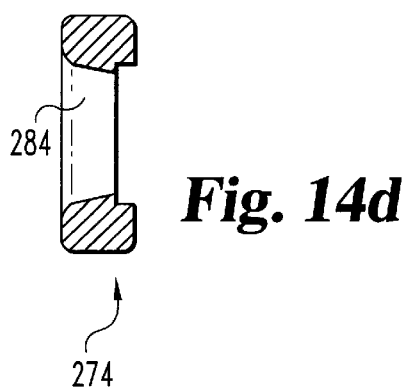
Figure 15A:
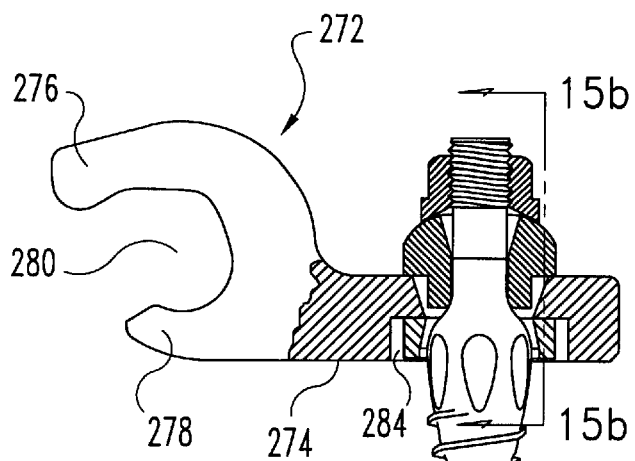
FIG. 15a is a partial cut-away view of the embodiment of the rod-bolt connector illustrated in FIG. 14a with embodiments of a bone bolt, washer, nut and stabilizer of the present invention.
Figure 15B:
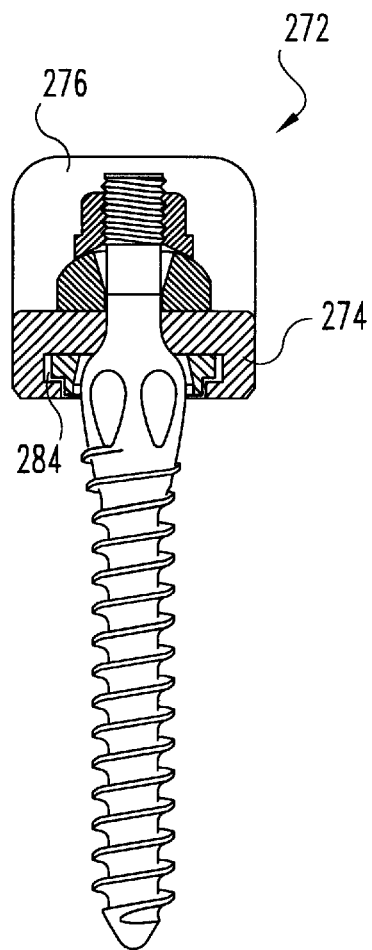

Referring now generally to FIGS. 13a–c, nut 250 of the present invention is illustrated. Nut 250 includes outer torque application surfaces 252 and an aperture 254 extending longitudinally through nut 250. Aperture 254 includes threads 256, which extend from the top of nut 250 toward the bottom of nut 250. Aperture 254 widens near the bottom of nut 250, and is bounded by walls 258. In a preferred embodiment, walls 258 are substantially spherical. However, other configurations are contemplated, such as conical.

In use, elongated member 100, washers 130 and 132, bolt 200, screw 230 and nut 250 are used in connection with stabilizer 26 or 115 as follows. In vertebrae, long bones, or other bone tissue, holes are drilled into the tissue for engagement of bone bolts 200 via cancellous threads 208. Bolts 200 are threaded into the drilled holes, and when bolts 200 are satisfactorily seated. Elongated member 100 is placed over bolts 200, so that proximal portions 204 of bolts 200 extend through slot 108 and bore 120, respectively. In the embodiment in which stabilizer 26 is placed in slot 108 on ledge 114 of elongated member 100 the proximal portion 204 of one bolt 200 extends through the aperture of stabilizer 26 as well. When elongated member 100 is properly placed, the sides of slot 108 are preferably adjacent to one or more flat portions 220 of one bolt 200.

Washer 130 is then fitted so that the bolt 200 extending through slot 108 also extends through aperture 142 of washer 130, projection 138 of washer 130 fits within slot 108 and on top of ledge 112 of elongated member 100, and downwardly-extending flanges 152 and 154 fit within slot 110 of elongated member 100. Positioned thusly, washer 130 is not able to rotate about bolt 200 due to the engagement of projection 138 with slot 108 and flanges 152 and 154 with slot 110. Washer 132 is fitted over the bolt 200 within bore 120, so that underside projection 164 of washer 132 rests on ledge 124 within bore 120, and such that aperture 176 of washer 132 and bore 128 of elongated member 100 are roughly aligned.

Holes may be drilled through bore 128 and slot 110 for screws 230. Alternatively, holes for screws 230 may be drilled prior to fitting washers 130 and 132 to elongated member 100, or may be drilled at the same time holes for bolts 200 are drilled. A bone screw 230 is threaded into a hole in the bone tissue through aperture 176, washer 132, and bore 128 at inferior end 104 of elongated member 100, and a separate screw 230 is threaded into a separate hole in the bone tissue through aperture 150 of washer 130 and slot 110 at superior end 102 of elongated member 100. As screw 230 is threaded into the bone, head 236 comes in contact with C-clip portion 174 of washer 132. Lower rounded surface 238 of screw 230, as the screw is threaded into the bone, pushes outward on tapered surface 178 of washer 132, forcing fingers 175*a* and 175*b* of C-clip portion 174 to open. When screw 230 is threaded far enough so that cylindrical portion 242 substantially passes tapered portion 178, fingers 175*a* and 175*b* of C-clip portion 174 close together, thereby preventing screw 230 from backing out under loads. In one embodiment, the closing of fingers 175*a* and 175*b* produce a positive feedback, such as an audible "click" apprising the surgeon that the screw has been sufficiently threaded. A similar or identical procedure is used to thread a second screw 230 into bone tissue through washer 130 and slot 108. C-clip portions 174 and 148 can be "tuned" to produce somewhat different sounds and/or to alter the strength of portions 174 and 148 and thereby alter the backing-out or threading force required to pass cylindrical portion 242 of screw 230 backward or forward through portions 174 or 148. This can be accomplished by making C-clip portions 174 and 148, and particularly fingers 175*a* and 175*b* and 149*a* and 149*b* thereof, thicker or thinner or by placing aperture 176 or 150 eccentrically with respect to washer 132 or 130 respectively.

When it is determined that elongated member 100 is in the proper position with respect to bolts 200 and/or screws 230, nuts 250 are threaded onto threaded portions 212 of bolts 200. Surface 258 of one nut 250 is generally configured with a substantially similar shape to head 162 of washer 132, and surface 258 of a second nut 250 is generally configured with a substantially similar shape to head 136 of washer 130. Thus, as nuts 250 are torqued onto bolts 200, respective surfaces 258 are pressed against surfaces 136 and 162 in a close fit. If desired, upper surfaces 216 may be engaged by a tool during nut tightening to resist rotation of the bolt and after nut tightening torque may be applied to surfaces 216 to shear off the post.

Elongated member 100 may be positioned with respect to bolts 200 such that the longitudinal axes of bolts 200 are not perpendicular to sides 100*a* or 100*b*. Wall portion 144 of washer 130 and wall portion 170 of washer 132 are tapered, as noted above, to accommodate the positioning of a bolt 200 along a variety of angles with respect to elongated member 100. Further, wall surface 96 of a stabilizer 26 placed within slot 108 on ledge 114 of elongated member 100 also accommodates the angle of a bolt 200. In the case in which a bolt 200 is not perpendicular with respect to slot 108 and/or bore 120, nut 250 is not squarely on top of head 162 or 136 of washer 132 or 130, but is off to one side. In that situation, surface 258 of nut 250 and head 162 or 136 may still be pressed together in a close fit due to the similar or identical configurations of surface 258 and heads 162 and 136.

Alternate embodiments of the structures disclosed herein are considered to be within the present invention. For example, tabs 152 and 154 on washer 130 may be left out as long as underside portion 138 of washer 130 and slot 108 of elongated member 100 are configured to prevent rotation of washer 130 with respect to elongated member 100 when washer 130 is engaged to elongated member 100. Further, it is contemplated that differing sizes of parts or of apertures within parts are within the present invention. Moreover, underside projections 164 and 138 of washers 132 and 130 are depicted as having a particular spatial and angular relationship with extension portion 166 and 140 of washers 132 and 130. Alternate embodiments of this configuration are considered to be within the scope of the present invention, e.g. placing extension portion 166 and 140 directly to one side of underneath projection 164 or 138, rather than placed off a corner of such projections.

Referring generally to FIGS. 14*a*–15*b*, there is shown an embodiment of a rod-bolt connector 270. Connector 270 includes a roughly C-shaped portion 272 and an extension portion 274. C-shaped portion 270 includes an upper portion 276 and a lower portion 278 defining an opening 280 into which a rod (not shown) can be fitted. Upper portion 276 includes a threaded bore 282 into which a set screw or other threaded piece (not shown) can be fitted to hold the rod within opening 280. Extension portion 274 includes a slot 284 which is configured substantially similarly to slot 108 of elongated member 100 and/or slot 30 of elongated member 22. Connector 270 can be used with bone bolt embodiments such as bone bolt 40 or 200, washer embodiments such as washers 42, 130 or 132, nut embodiments such as nuts 44 or 250, and stabilizer embodiments such as stabilizers 26 or 115, as further illustrated in FIGS. 15*a*–15*b*.

The parts of the implant system of the present invention may be made available in the form of kits containing a plurality of sizes and configurations of a single part, or a plurality of sizes and configurations of all parts that can be included in the system of the present invention. Such kits may include, for example, a set of elongated members 22 and/or 100 of various lengths and having differing numbers or orientations of slots and/or bores. In the case of elongated member 100, a kit could include a set of elongated member having varying degrees of bend along longitudinal axis 106. Sets of washers, bolts, screws and nuts as disclosed herein can also be provided. Further, tools such as wrenches and screwdrivers compatible with the parts of the implant system of the present invention may also be included.

The devices of the present invention are preferably constructed of sturdy bio-compatible materials, such as stainless steel, titanium, certain plastics, or other known materials.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. An orthopedic implant, comprising:
   a longitudinal member, said longitudinal member having a lower side for facing a bone, an upper side for facing away from a bone, and an aperture through said longitudinal member from said first side to said second side, said longitudinal member further including a longitudinal channel parallel to and between said first and second sides, said channel being substantially perpendicular to said aperture;
   a stabilizer having an opening therethrough bounded by a conical surface, said stabilizer further having a plurality of laterally extending fingers occupying said channel so that said stabilizer is in one of an infinite number of positions wherein said opening is adjacent to said aperture of said longitudinal member;

a fixation member having a first threaded portion for fixing to a bone, a second threaded portion, and a diametrally enlarged portion between said first and second threaded portions, said enlarged portion including a plurality of torque transmission surfaces, and said fixation member extending through said stabilizer and said longitudinal member so that said enlarged portion contacts a portion of said surface bounding said opening of said stabilizer;

a washer having a rounded top, said washer adapted for placement over said second threaded part of said fixation member and into contact with said second side of said longitudinal member; and a nut having a rounded underside and adapted to be threaded onto said second threaded portion of said fixation member and down onto said washer, to thereby lock said fixation member in place relative to said longitudinal member.

2. The implant of claim 1, wherein said channel is continuous and extends through substantially the entire length of said longitudinal member.

3. The implant of claim 1, further comprising at least one additional stabilizer each having an opening therethrough bounded by a conical surface, said at least one additional stabilizer further each having a plurality of lateral fingers occupying said channel so that said at least one additional stabilizer is in a preselected one of an infinite number of positions wherein said opening of said at least one additional stabilizer is adjacent to said aperture of said longitudinal member.

4. The implant of claim 3, further comprising at least one additional fixation member each having a first threaded portion for fixing to a bone, a second threaded portion, and a diametrally enlarged portion between said first and second threaded portions, said enlarged portion of said at least one additional fixation member including a plurality of torque transmission surfaces, and said at least one additional fixation member extending through a corresponding one of said at least one additional stabilizer and said longitudinal member so that said enlarged portion of said at least one additional fixation member contacts a portion of said surface bounding said opening of said corresponding stabilizer.

5. The implant of claim 1, wherein said opening in said stabilizer has a longitudinal axis, and said stabilizer substantially forms a parallelogram in a plane substantially perpendicular to said axis.

6. The implant of claim 5, wherein said stabilizer substantially forms a square in a plane substantially perpendicular to said axis.

7. The implant of claim 1, wherein said washer has a bottom surface for contacting said longitudinal member that includes a substantially flat portion and a projection extending substantially perpendicularly from said bottom surface.

8. The implant of claim 7, wherein said longitudinal member has a ledge within said aperture and said aperture is bounded above said ledge by substantially parallel wall sections, and said projection of said washer is configured to fit within said aperture and rest on said ledge.

9. The implant of claim 8, wherein said projection of said washer is configured to cooperate with said substantially parallel wall sections to minimize rotation of said washer with respect to said longitudinal member.

10. The implant of claim 9, wherein said projection is substantially square.

11. The implant of claim 7, wherein said washer includes a hole therethrough bounded by a wall that has a conical portion.

12. The implant of claim 1, wherein said nut includes a break-off portion that is severed when a torque exceeding a predetermined amount is applied to said break-off portion.

13. A spinal implant system, comprising:

a plate member having a longitudinal axis, a first end and a second end, said first end having a first slot and a second slot extending through said plate member, said slots being substantially parallel to and offset from said axis and said first slot having a longitudinal channel formed therein, said second end having a first aperture and a second aperture through said plate member;

a stabilizer having an opening therethrough bounded by a conical surface, said stabilizer further having a plurality of lateral fingers occupying said channel so that said stabilizer is in a preselected one of an infinite number of positions wherein said opening is adjacent to said first slot;

a fixation member having a first threaded portion for connection with a bone, a second threaded portion, and an enlarged head portion between said threaded portions for spacing said stabilizer and said plate member from said bone, said fixation member extending through said opening of said stabilizer and said first slot;

a washer having a body portion with a convex upper portion, a substantially flat lower surface, and a hole therethrough, said washer further including a flange portion extending laterally from said body portion, said flange including a C-clip, said washer being adapted for placement around said fixation member so that said C-clip extends above a portion of said second slot; and a nut having a concave underside, said nut being threaded on said second threaded portion of said fixation member, whereby said plate member, stabilizer, fixation member, washer and nut are locked in cooperation with each other.

14. The system of claim 13, further comprising a screw having a threaded portion and a head portion, said head portion having a lower convex portion, an upper portion, and a substantially cylindrical portion between said upper and lower portions; and said screw extending through said C-clip and said second slot and into a bone.

15. The system of claim 14, wherein said second slot has a beveled upper edge adapted to accommodate said lower convex portion of said head portion of said screw.

16. The system of claim 14, wherein said C-clip has an inner diameter smaller than the diameter of said cylindrical portion of said head portion of said screw.

17. The system of claim 14, wherein said lower convex portion of said head of said screw is spherical.

18. The system of claim 17, wherein said upper portion of said head of said screw is spherical.

19. The system of claim 14, wherein said screw has a longitudinal axis, said upper portion and said lower portion of said head have respective maximum diameters with respect to said screw axis, and said diameter of said cylindrical portion is greater than said diameters of said upper portion and said lower portion.

20. The system of claim 19, wherein said head portion of said screw includes a tool-insertion recess.

21. The system of claim 13, wherein said enlarged head portion of said fixation member has a plurality of substantially flat torque transmission surfaces.

22. The system of claim 13, wherein said enlarged portion of said fixation member overlaps with one of said threaded portions.

23. The system of claim 22, wherein said first threaded portion of said fixation member has a head surface and a root diameter that increases toward said enlarged head portion so that said head surface is substantially a continuation of said root diameter.

24. The system of claim 13, wherein said flange portion of said washer is non-parallel with said substantially flat lower surface.

25. The system of claim 24, wherein said flange portion of said washer forms an obtuse angle with said substantially flat lower surface.

26. The system of claim 13, wherein said flange portion includes lower surface and a secondary flange extending from said lower surface.

27. The system of claim 13, wherein said hole through said body portion of said washer is bounded by a wall having a conical upper portion.

28. The system of claim 13, further comprising
   a second fixation member having a first threaded portion for connection with a bone, a second threaded portion, and an enlarged head portion between said threaded portions, said second fixation member extending through said first aperture and into a bone,
   a second washer having a body portion with a convex upper portion, a substantially flat lower surface, and a hole therethrough, said washer further including a flange portion extending laterally from said body portion, said flange including a C-clip, said washer being adapted for placement around said second fixation member so that said C-clip extends above a portion of said second aperture, and
   a second nut having a concave underside, said nut being threaded on said second threaded portion of said second fixation member, whereby said plate member, second fixation member, second washer and second nut are locked in cooperation with each other.

29. The system of claim 28, further comprising a second screw having a threaded portion and a head portion, said head portion having a lower convex portion, an upper portion, and a substantially cylindrical portion between said upper and lower portions; and
   said second screw extending through said C-clip and said second aperture and into a bone.

30. The system of claim 29, wherein said C-clip has an inner diameter smaller than the diameter of said cylindrical portion of said head portion of said screw.

31. The system of claim 13, wherein said second threaded portion includes a break-off groove.

32. The system of claim 31, wherein said second threaded portion includes an end portion having a driving print thereon.

33. The system of claim 32, wherein said driving print includes a plurality of external surfaces for torque transmission.

34. The system of claim 13, wherein said C-clip portion of said washer is integrally formed with said flange portion.

* * * * *